United States Patent [19]

Kinast et al.

[11] 4,348,402

[45] Sep. 7, 1982

[54] 2-HYDROXYALKYL-3,4,5-TRIHYDROXY-PIPERIDINE COMPOUNDS, THEIR PRODUCTION AND THEIR MEDICINAL USE

[75] Inventors: Günther Kinast; Lutz Müller; Rüdiger Sitt; Walter Puls, all of Wuppertal, Fed. Rep. of Germany

[73] Assignee: Bayer Aktiengesellschaft, Leverkusen, Fed. Rep. of Germany

[21] Appl. No.: 193,498

[22] Filed: Oct. 2, 1980

[30]  Foreign Application Priority Data

Oct. 19, 1979 [DE] Fed. Rep. of Germany ....... 2942365

[51] Int. Cl.³ .................. A61K 31/445; C07D 211/42
[52] U.S. Cl. .................... 424/267; 542/469;
546/242; 546/243; 546/219; 546/198; 536/17.2
[58] Field of Search ........... 546/219, 242, 243; 542/469; 424/267

[56]  References Cited

U.S. PATENT DOCUMENTS 4,260,622  4/1981  Junge et al. .................. 546/219

FOREIGN PATENT DOCUMENTS 947       8/1978  European Pat. Off. ........... 546/219
70955B/39 8/1979  Japan ................................ 546/242
15365C/09 1/1980  Japan ................................ 546/242

OTHER PUBLICATIONS

Chemical Abstracts, vol. 66, 1967, abstracting Inouye et al. in J. Antibiotics, (Tokyo), Series A, vol. 19, No. 6, pp. 288–292, (1966).
Inouye et al., "Tetrahedron", vol. 23, pp. 2125–2144, (1968).
Paulser et al., "Chem. Berichte", JAAR 100, pp. 512–520, (1967).
Hanesslan, "Chemistry and Industry", (1966), Dec. 17, vol. 51, pp. 2126–2127.

Primary Examiner—Robert T. Bond

[57]  ABSTRACT

The invention relates to α-hydroxyalkyl-3,4,5-trihydroxypiperidines defined by Formula (I), infra, and pharmaceutical compositions and medicaments containing said compounds. Also included in the invention are methods for the use of said compounds, compositions and medicaments as inhibitors of α-glucoside hydrolases; and intermediates for the compounds of said Formula (I).

19 Claims, No Drawings

2-HYDROXYALKYL-3,4,5-TRIHYDROXY-PIPERIDINE COMPOUNDS, THEIR PRODUCTION AND THEIR MEDICINAL USE

The present invention relates to certain new 2-hydroxyalkyl-3,4,5-trihydroxypiperidine compounds, to processes for their production and to their use as medicaments, in particular against diabetes, hyperlipoproteinameia, arteriosclerosis and adiposity.

It has already been disclosed that N-alkyl and N-alkenyl derivatives of 2-hydroxymethyl-3,4,5-trihydroxypiperidine are potent inhibitors for α-glucoside hydrolases (see European Published Patent Application 947).

According to the present invention there are provided compounds which are 2-hydroxyalkyl-3,4,5-trihydroxypiperidines of the formula

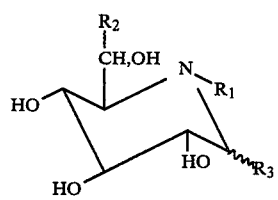

in which
$R_1$ denotes a hydrogen atom or a saturated or unsaturated optionally substituted aliphatic radical,
$R_2$ denotes an optionally substituted alkyl, alkenyl, or aryl radical and
$R_3$ denotes a hydrogen atom or a sulpho or hydroxyl group.

The new compounds of the present invention have an increased action on α-glucoside hydrolases.

According to the present invention there are provided a process for the production of a compound of the present invention in which (a) a compound of the formula

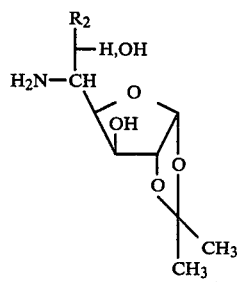

in which
$R_2$ has the abovementioned meaning,
is reacted with sulphur dioxide to give a compound of the formula (I) in which $R_1$ denotes a hydrogen atom and $R_3$ denotes an SO$_3$H group;
this resulting compound is reacted, if desired, with a base or a basic ion exchanger to give a compound of the formula (I) in which $R_3$ denotes an OH group;
this resulting compound is reduced, if desired, to give a compound of the formula (I) in which $R_1$ and $R_3$ denote hydrogen atoms; and
this resulting compound is subjected, if desired, to reductive alkylation with an aldehyde or to alkylation with an alkyl halide to give a compound of the formula (I) in which $R_3$ denotes a hydrogen atom and $R_1$ has an abovementioned meaning, with the exception of hydrogen, or (b) where a compound of formula (I) in which $R_1$ and $R_3$ denote hydrogen atoms is desired, a compound of the formula

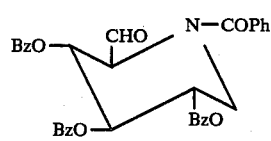

in which
Bz denotes

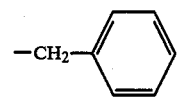

and Ph denotes a phenyl radical,
is reacted with a compound R$_2$MgX, in which R$_2$ has the same meaning as in formula (I) and X denotes a halogen atom, and reacting the resulting compound of the formula

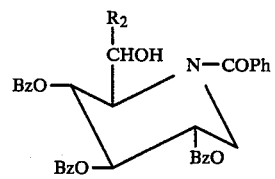

in which Bz, Ph and R$_2$ have the abovementioned meanings, with sodium in liquid ammonia to give the following resulting compound of the formula

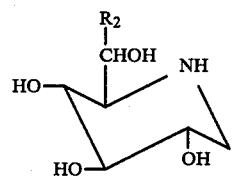

in which
R$_2$ has the abovementioned meaning.

A process for the production of compounds of the formula (II), using the starting compounds shown, is illustrated by the following equation:

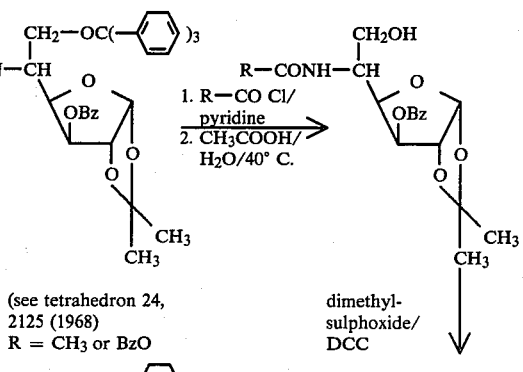

(see tetrahedron 24, 2125 (1968)
R = CH$_3$ or BzO

Bz = —CH$_2$—⟨phenyl⟩ dimethyl-sulphoxide/DCC

-continued

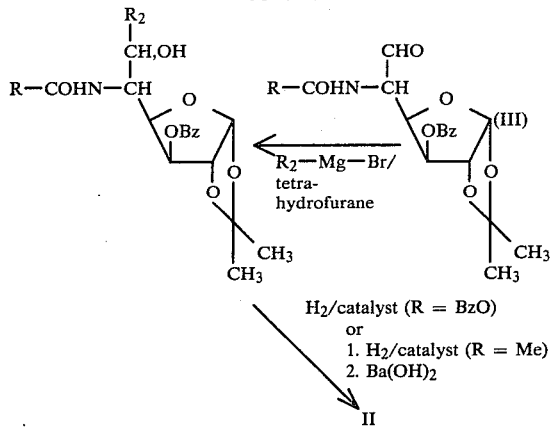

A benzyloxycarbonyl or acetyl radical, for example, can be used as a protective group for the amino group. The compounds of the formula III in which R denotes $CH_3$ or BzO— are important intermediate compounds for the preparation of the compounds of formula (I) of the present invention. They are a further subject of the present invention.

Examples of these novel intermediate compounds and their production are given in the preparative Examples.

Further details of reaction variant (a), now follow.

The step of reacting compounds of formula (II) with $SO_2$ with splitting off of the isopropylidene group and formation of the piperidine ring is generally carried out by a procedure in which an aqueous or water-containing alcoholic solution of the compounds of the formula (II) is saturated with $SO_2$ and kept at temperatures between 20° C. and 50° C. for several days. The compounds of the formula (I) are then obtained as bisulphite adducts (in which $R_3$ denotes $-SO_3H$), which in most cases crystallise well and from which the compounds of the formula (I) (in which $R_3$ denotes $-OH$) can be liberated in a further step with the aid of, for example, aqueous $Ba(OH)_2$.

The step of reducing compounds of the formula (I) in which $R_3$ denotes OH to give compounds of the formula (I) in which $R_3$ denotes a hydrogen atom is generally carried out using alkali metal borohydrides, alkali metal cyanoborohydrides or dialkylaminoboranes in which each alkyl group preferably contains 1 to 4 carbon atoms. It is preferable to use sodium cyanoborohydride in aqueous solution or in a water-miscible water-containing organic solvent, such as methanol, at room temperature or if appropriate elevated temperature. However, the reduction is very particularly preferably carried out catalytically with Pt or Pd as the catalyst or in the presence of Raney nickel. This procedure is preferably carried out in aqueous solution at room temperature.

Alkali metal cyanoborohydrides, dialkylaminoboranes and alkali metal borohydrides may be used as hydrogen donor reducing agents for the reductive alkylation step. It is particularly preferable to use sodium cyanoborohydride in this process variant. The reaction is in general carried out at temperatures between $-20°$ C. and room temperature. However, it may also be favourable to heat the mixture to the reflux temperature.

The reductive alkylation step is usually carried out in an inert solvent. Although anhydrous aprotic solvents can be employed (for example tetrahydrofurane, if the reducing agent is morpholinoborane), a protic solvent is nevertheless usually employed. Particularly suitable protic solvents are $C_1-C_6$ alkanols. However, it is also possible to use water or an aqueous $C_1-C_6$ alkanol (for example aqueous methanol or ethanol) or other aqueous solvent systems, such as aqueous dimethylformamide, aqueous hexamethylphosphoric acid triamide, aqueous tetrahydrofurane or aqueous ethylene glycol dimethyl ether.

The reductive alkylation step is usually carried out in a pH range from 1 to 11, and a pH range from 4 to 7 is preferred.

The alkylation step is illustrated by the following equation using the reactants indicated:

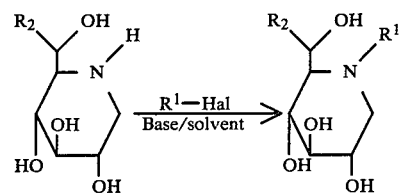

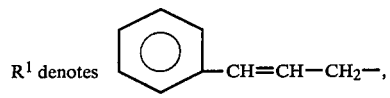

$$CH_3-CH=CH-CH=CH-CH_2-, CH_3-CH=CH-CH_2-$$

"Hal" denotes Br, I, Cl, O-mesyl or O-tosyl
"base" denotes $K_2CO_3$, NaOH or KOH
"solvent" denotes dimethylformamide, dimethylsulphoxide or mixtures thereof with $H_2O$.

In reaction variant (b) the aldehyde of formula (IV) employed can be prepared by oxidising the corresponding alcohol with dicyclohexylcarbodiimide in dimethylsulphoxide in the presence of phosphoric acid.

The two processes for the production of compound IV are illustrated by the following equations:

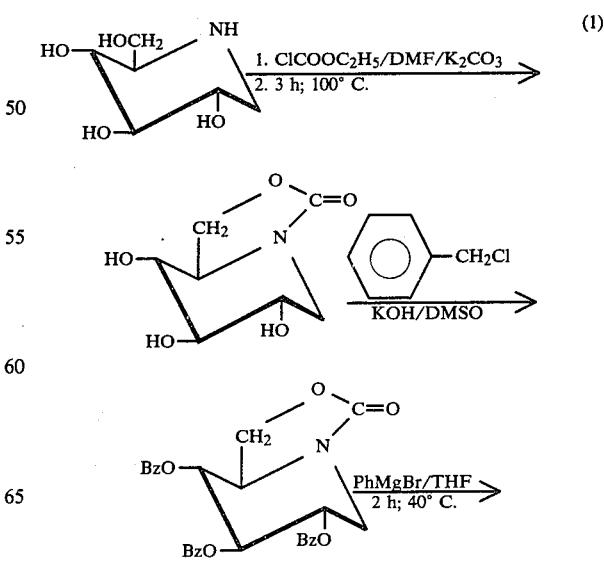

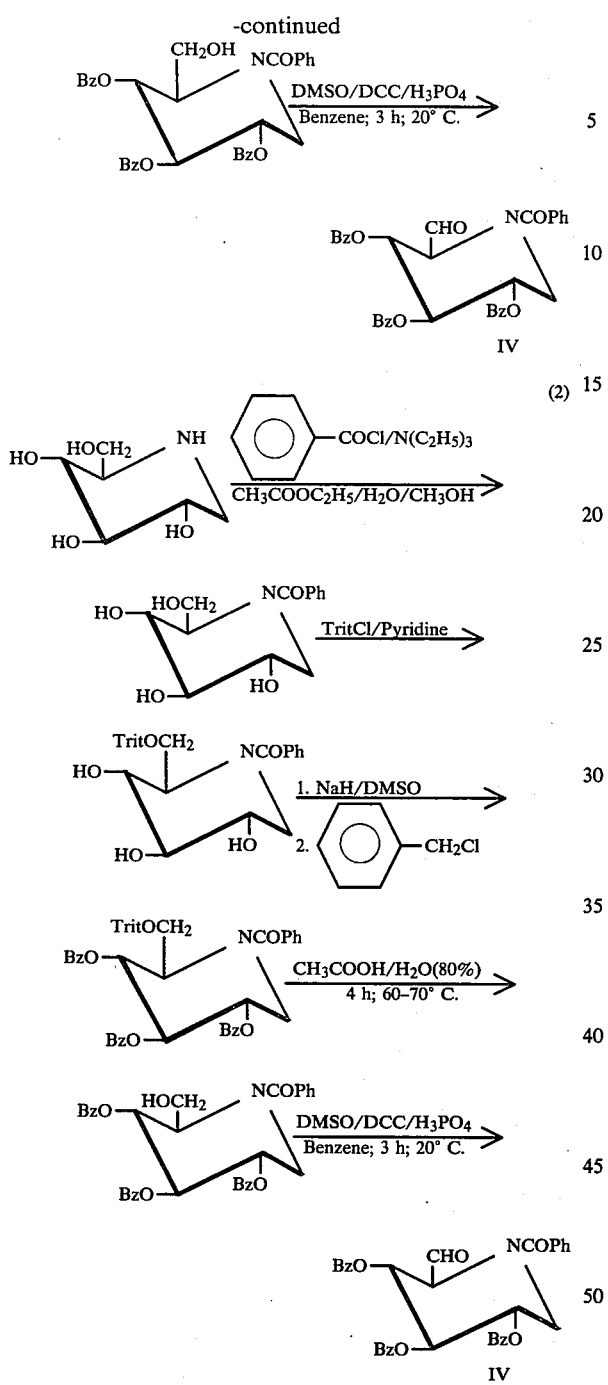

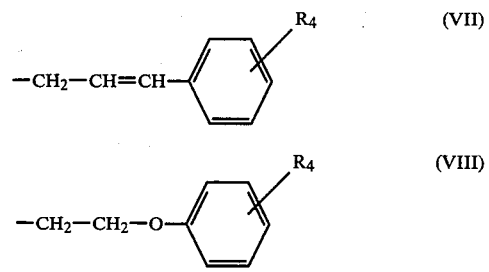

in which

R₄ denotes a hydrogen or halogen (preferably fluorine, chlorine or bromine) atom or a C₁ to C₄ alkyl, C₁ to C₄ alkoxy, nitro or cyano radical, R₂ denotes a C₁ to C₁₀ alkyl, C₂ to C₆ alkenyl or C₄ to C₁₀ alkadienyl radical which is optionally substituted by hydroxyl, C₁ to C₄ alkoxy or phenyl, which can in turn be substituted by C₁ to C₄ alkyl, C₁ to C₄ alkoxy, halogen (preferably fluorine, chlorine or bromine), nitro or cyano, or denotes a phenyl radical which is optionally substituted by C₁ to C₄ alkyl, C₁ to C₄ alkoxy, halogen, (preferaably fluorine, chlorine or bromine), nitro, or cyano, and R₃ has the above-mentioned meaning.

Particularly preferred compounds of formula (I) of the present invention are those in which R₁ denotes a hydrogen atom or a C₁ to C₁₀ alkyl, hydroxyethyl, phenoxyethyl, allyl, but-2-enyl, penta-2,4-dienyl, hexa-2,4-dienyl, hepta-2,4-dienyl or

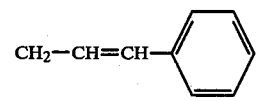

radical, R₂ denotes a C₁ to C₆ alkyl, allyl, benzyl or phenyl radical, and R₃ has the abovementioned meaning.

Very particularly preferred compounds of formula (I) of the present invention are those in which R₁ denotes a hydrogen atom or a methyl, ethyl, propyl, hexyl, allyl, 2-propen-1-yl, 2,4-hexadien-1-yl, cinnamyl or 2-phenoxyethyl radical, R₂ denotes a methyl or ethyl radical and R₃ denotes a hydrogen atom, or R₁ denotes a hydrogen atom, R₂ denotes a methyl radical and R₃ denotes a sulpho or hydroxyl radical.

The inhibitors according to the invention are suitable as therapeutic agents for the following indications in warm-blooded animals: prediabetes, gastritis, constipation, caries, infections of the gastro-intestinal tract, meteorism, flatulence, hypertension and, in particular, arteriosclerosis, adiposity, diabetes and hyperlipoproteinaemia.

The combining of inhibitors for glycoside hydrolases which complement one another in their action may be recommended to broaden the action spectrum, these being either combinations of the inhibitors according to the invention with one another or combinations of the inhibitors according to the invention with inhibitors which are already known.

In some cases, combinations of the inhibitors according to the invention with known oral antidiabetic agents (β-cytotropic sulphonylurea derivatives and/or biguanides which have an action on the blood sugar level) and with active compounds which lower the blood lipid Compound IV, the corresponding alcohol and N,7-O-Cyclocarbamato-2-hydroxymethyl-3,4,5-trihydroxypiperidine are important intermediate compounds for the preparation of the compounds of formula I of the present invention.

These three compounds and their preparation are therefore a further subject of the present invention.

Preferred compounds of formula (I) of the present invention are those in which R₁ denotes a hydrogen atom, a C₁ to C₁₀ alkyl, C₃ to C₆ alkenyl or C₅ to C₁₀ alkadienyl radical which is optionally substituted by hydroxyl or C₁ to C₄ alkoxy, or a radical of the general formula level, such as, for example, clofibrate, nicotinic acid, cholestyramine and others, are also advantageous.

The compounds can be administered without dilution, for example as powders or in a gelatin casing, or in a pharmaceutical composition in combination with an excipient.

As stated above, the invention also relates to the use in medicine of the compounds of the invention.

The present invention provides pharmaceutical compositions containing as active ingredients a compound of the invention in admixture with an inert pharmaceutical carrier, e.g. a solid or liquefied gaseous diluent, or in admixture with a liquid diluent other than a solvent of a molecular weight less than 200 (preferably less than 350) except in the presence of a surface active agent.

The invention further provides pharmaceutical compositions containing as active ingredients a compound of the invention in the form of a sterile and/or physiologically isotonic aqueous solution.

The invention also provides medicaments in dosage unit form comprising a compound of the invention.

The invention also provides medicaments in the form of tablets (including lozenges and granules), dragees, capsules, pills, ampoules or suppositories comprising a compound of the invention.

"Medicament" as used in this Specification means physically discrete coherent portions suitable for medical administration. "Medicament in dosage unit form" as used in this Specification means physically discrete coherent units suitable for medical administration each containing a daily dose or a multiple (up to four times) of submultiple (down to a fortieth) of a daily dose of the compound of the invention in association with a carrier and/or enclosed within an envelope. Whether the medicament contains a daily dose or, for example, a half, a thrid or a quarter of a daily dose will depend on whether the medicament is to be administered once or, for example, twice, three times or four times a day respectively.

The pharmaceutical composition according to the invention may, for example, take the form of suspensions, solutions and emulsions of the active ingredient in aqueous or non-aqueous diluents or syrups.

The pharmaceutical compositions according to the invention generally contain from 0.1% to 99.5% of the active ingredient by weight of the total composition.

In addition to a compound of the invention, the pharmaceutical compositions and medicaments according to the invention can also contain other pharmaceutically active compounds. They may also contain a plurality of compounds of the invention.

Any diluent in the medicaments of the present invention may be any of those mentioned above in relation to the pharmaceutical compositions of the present invention. Such medicaments may include solvents of molecular weight less than 200 as sole diluent.

The discrete coherent portions constituting the medicament according to the invention will generally be adapted by virtue of their shape or packaging for medical administration and may be, for example, any of the following: tablets (including lozenges and granulates), pills, dragees, capsules, suppositories and ampoules. Some of these forms may be made up for delayed release of the active ingredient. Some, such as capsules, include a protective envelope which renders the portions of the medicament physically discrete and coherent.

The preferred dialy dose for administration of the medicaments of the invention is 25 mg to 500 mg of active ingredient.

The product of the above-mentioned pharmaceutical compositions and medicaments is carried out by any method known in the art, for example, by mixing the active ingredient(s) with the diluent(s) to form a pharmaceutical composition (e.g. a granulate) and then forming the composition into the medicament (e.g. tablets).

This invention further provides a method of combating the above-mentioned diseases in warm-blooded animals, which comprises administering to the animals a compound of the invention alone or in admixture with a diluent or in the form of a medicament according to the invention.

In general it has provided advantageous to administer amounts of from 0.05 mg to 10 mg/kg of body weight per day, usually at all the main meal times and secondary meal times during the day, to achieve effective results. Nevertheless, it can at times be necessary to deviate from those dosage rates, and in particular to do so as a function of the nature and body weight of the warm-blooded animal subject to be treated, the individual reaction of this subject to the treatment, the type of formulation in which the active ingredient is administered and the mode in which the administration is carried out, and the point in the progress of the disease or interval at which it is to be administered. Thus it may in some case suffice to use less than the above-mentioned minimum dosage rate, whilst other cases the upper limit mentioned must be exceeded to achieve the desired results. Where larger amounts are administered it can be advisable to divide these into several individual administrations over the course of the day.

The compounds according to the invention are formulated and administered in the same manner as that described in European Published Patent Application 947.

The following examples illustrate processes for the production of compounds of the present invention.

EXAMPLE 1

(a)

5-Acetamido-3-O-benzyl-5-desoxy-1,2-O-isopropylidene-6-O-triphenylmethyl-α-D-glucofuranose 551 g of 5-amino-5-desoxy-3-O-benzyl-1,2-O-isopropylidene-6-O-triphenylmethyl-α-D-glucofuranose (see S. Inouye, T. Tsurnoka, T. Ito and T. Nidda, Tetrahedron 24, 2125–2144 (1968)), 400 ml of methylene chloride, 400 ml of pyridine and 200 ml of acetic anhydride were brought together at 0°–20° C. and the mixture was stirred at room temperature for 24 hours. The methylene chloride was then stripped off in vacuo, 300 g of ice were added to the residue and the mixture was stirred for 30 minutes. It was extracted three times with 300 ml of chloroform each time and the extract was washed twice with water and twice with sodium bicarbonate solution, dried over sodium sulphate and concentrated in vacuo at a bath temperature of 40° C. Yield: 600 g.

(b)

5-Acetamido-3-O-benzyl-5-desoxy-1,2-O-isopropylidene-α-D-glucofuranose 600 g of crude 5-acetamido-5-desoxy-3-O-benzyl-1,2-O-isopropylidene-6-O-triphenylmethyl-α-D- glucofuranose were dissolved in 1.5 ml of glacial acetic acid, 600 ml of water were added and the mixture was stirred at 70° C. for 2 hours and at 20° C. overnight. The reaction was followed by thin layer chromatography (chloroform/ethyl acetate 3:1 and chloroform/methanol 10:1). The precipitate was filtered off, washed with glacial acetic acid/water 1:1 and discarded. The comined filtrates were evaporated at 50° C. in vacuo. The residue was taken up in 1 liter of ethyl acetate, insoluble constituents were filtered off and the ethyl acetate phase was washed with water and with sodium bicarbonate solution until neutral, dried over sodium sulphate and evaporated in vacuo. The resulting oil crystallised from methanol/water, yield: 101 g of melting point 84°–88° C. The mother liquor was evaporated, the residue was taken up in a little ether, the mixture was discharged onto a silica gel column and the column was eluted successively with 6 liters of ether, 5 liters of ethyl acetate and 2.5 liters of methanol. The ether eluate was discarded, the ethyl acetate eluate and the methanol eluate were each evaporated and the residue was crystallised from methanol/water. A total of 214 g (61%) of melting point 84°–88° C. was obtained.

(c)
5-Acetamido-3-O-benzyl-5-desoxy-1,2-O-iso-propylidene-α-D-glucofuranose 51 g of 5-acetamido-6-O-acetyl-3-O-benzyl-5-desoxy-1,2-O-isopropylidene-α-D-glucofuranose (see H. Saeki et al, Chem. Pharm. Bull 26, 2477 (1968)), 160 ml of methanol and 0.2 g of sodium methylate were stirred at room temperature overnight. The batch was then neutralised with $CO_2$ (dry ice) and evaporated in vacuo, the residue was taken up in ethyl acetate, the ethyl acetate mixture was washed twice with water, dried over sodium sulphate and evaporated in vacuo and the residue was crystallised from ether/petroleum ether. Yield: 43 g (94% of theory) of melting point 88° C.

(d)
5-Acetamido-3-O-benzyl-5-desoxy-1,2-O-isopropylidene-α-D-gluco-hexodialdo-1,4-furanose:

21 g of 5-acetamido-3-O-benzyl-5-desoxy-1,2-O-isopropylidene-α-D-glucofuranose, 54 ml of dimethylsulphoxide. 15 ml of benzene, 3 g of phosphoric acid and 37.5 g of dicyclohexylcarbodiimide were brought together, whilst cooling with ice, and the mixture was stirred at 20°–25° C. for 3 hours. For working up, 12 g of oxalic acid were slowly added, the mixture was stirred for 30 minutes, the precipitate was filtered off and washed with ethyl acetate, the filtrate was washed with 50 ml of saturated sodium bicarbonate solution and the aqueous phase was washed three times with 50 ml of ethyl acetate each time. The combined ethyl acetate extracts were dried over sodium sulphate, washed twice with saturated sodium chloride solution, dried twice over sodium sulphate and evaporated at 20° C. in vacuo. The resulting crude product (19 g) was immediately reacted further.

(e)
5-Acetamido-3-O-benzyl-5,7-didesoxy-1,2-O-isopropylidene-D(L)-glycero-α-D-glucohepto-1,4-furanose:

39 ml of methyl iodide in 300 ml of anhydrous ether were added dropwise to 16.7 g of magnesium filings in 50 ml of anhydrous ether such that the ether simmered, and the mixture was then boiled under refux for 30 minutes. 19 g of crude acetamido-3-O-benzyl-5-desoxy-1,2-O-isopropylidene-α-D-gluco-hexodialdo-1,4-furanose in 200 ml of anhydrous ether were added dropwise to this solution at 20°–25° C. and the mixture was stirred overnight at room temperature. 500 ml of 20% strength ammonium chloride solution were then carefully added, whilst cooling with ice, the ether phase was separated off and three extractions were carried out with 100 ml of ethyl acetate each time. The combined organic phases were washed with sodium bicarbonate solution, dried over sodium sulphate and evaporated in vacuo and the residue was recrystallised from isopropanol. Yield: 3.5 g of melting point 179°–181° C.

(f)
5-Amino-3-O-benzyl-5,7-didesoxy-1,2-O-isopropylidene-D(L)-glycero-α-D-glucohepto-1,4-furanose:

2.4 g of 5-acetamido-3-O-benzyl-5,7-didesoxy-1,2-O-isopropylidene-D(L)-glycero-α-D-glucohepto-1,4-furanose, 40 ml of ethylene glycol, 8 ml of water and 2 g of potassium hydroxide were heated to 150° C. for 3 hours. After cooling, the reaction mixture was neutralised with $CO_2$ and evaporated under a high vacuum, the residue was digested with hot ethanol, the solution was evaporated and the residue was purified by column chromatography on 250 g of silica gel using ammonia-saturated chloroform/ethanol 10:1. 1.9 g of the desired compound were obtained as an oil.

(g)
5-Acetamido-5,7-didesoxy-1,2-O-isopropylidene-D(L)-glycero-α-D-glucohepto-1,4-furanose:

20 g of 5-acetamido-3-O-benzyl-5,7-didesoxy-1,2-O-isopropylidene-D(L)-glycero-α-D-glucohepto-1,4-furanone were dissolved in 80 ml of methaol and 50 ml of glacial acetic acid and were hydrogenated on 15 g of 5% strength palladium-on-charcoal under 3.5 atmospheres at 30° C. for 8 hours. The batch was then filtered, the filtrate was concentrated in a rotary evaporator, the residue was taken up in ethyl acetate and the ethyl acetate mixture was washed with sodium hydroxide solution until neutral, dried and concentrated in a rotary evaporator. 13.7 g of an oil were obtained.

(h)
5-Amino-5,7-didesoxy-1,2-O-isopropylidene-D(L)-glycero-α-D-glucohepto-1,4-furanose:

13 g of 5-acetamido-5,7-didesoxy-1,2-O-isopropylidene-D(L)-glycero-α-D-glucohepto-1,4-furanose, 24.7 g of $Ba(OH)_2 \times 8H_2O$ and 180 ml of water were boiled under reflux overnight. 18 g of ammonium bicarbonate were then added, the mixture was stirred at room temperature for 2 hours, the precipitate was filtered off and washed with water, the filtrate was concentrated, the residue was discharged onto a column containing 250 ml of a strongly basic ion exchanger (Lewatit n 500) and the column was eluted with water. After concentrating the eluate in a rotary evaporator, the residue was recrystallised from chloroform. Yield: 8.5 g, melting point: 127°–131° C.

(i)
5-Amino-5,7-didesoxy-1,2-O-isopropylidene-D(L)-glycero-α-D-glucohepto-1,4-furanose:

4 g of sodium were added to 1.9 g of 6-amino-3-O-benzyl-5,7-didesoxy-1,2-O-isopropylidene-D(L)-glycero-α-D-glucohepto-1,4-furanose in 100 ml of liquid ammonia and the mixture was stirred at −70° C.

overnight. 6 g of ammonium chloride and 250 ml of methanol were then added, the mixture was allowed to warm to room temperature, the salts were filtered off, the filtrate was evaporated and the residue was chromatographed on 80 g of silica gel with a mixture of ethyl acetate/methanol/concentrated aqueous ammonia 100:60:2. The eluate was evaporated, the residue was taken up in hot isopropanol, the isopropanol mixture was filtered and the product was precipitated with three times the amount of petroleum ether. Yield: 0.6 g.

(j) Bisulphite adduct of 5-amino-5,7-didesoxy-D(L)-glycero-D-glucoheptose:

Sulphur dioxide was passed into a solution of 320 mg of 5-amino-5,7-didesoxy-1,2-O-isopropylidene-D(L)-glycero-α-D-glucohepto-1,4-furanose in 2 ml of water at room temperature for 20 hours and then at 40° C. for 20 hours. 20 ml of methanol were subsequently added, whereupon the desired product crystallised out. Yield 200 mg of melting point 128°–130° C.

(k) 5-Amino-5,7-didesoxy-D(L)-glycero-O-glucoheptose:

120 mg of the bisulphite adduct of 5-amino-5,7-didesoxy-D(L)-glycero-D-glucoheptose were dissolved in 5 ml of water, strongly basic ion exchangers were added, the mixture was stirred for 30 minutes and filtered, the residue was washed with water and the filtrate was evaporated in vacuo at 20° C. Yield: 70 mg.

(l) 1,5,7-Tridesoxy-1,5-imino-D(L)-glycero-D-glucoheptitol:

120 mg of the bisulphite adduct of 5-amino-5,7-didesoxy-D(L)-glycero-D-glucoheptose were dissolved in 15 ml of water, 173 mg of barium hydroxide $\times 8$ $H_2O$ and 400 mg of Raney nickel were added and hydrogenation was carried out at room temperature under 3 atmospheres for 7 hours. The reaction mixture was then filtered, the filtrate was evaporated in vacuo and the residue was purified by column chromtography on 20 g of silica gel with ether/methanol/concentrated aqueous ammonia (5:6:2). Yield 40.7 mg of an oil which crystallised within a few hours. Melting point: 165°–6° C.

(m) 1,5,7-Tridesoxy-1,5-imino-N-methyl-D(L)-glycero-D-glucoheptitol:

32 mg (0.18 mole) of 1,5,7-tridesoxy-1,5-imino-D(L)-glycero-D-gluco-heptitol were dissolved in 2 ml of methanol, 20 mg of sodium cyanoborohydride, 0.05 ml of formalin solution (40% strength) and 0.02 ml of glacial acetic acid were added and the reaction mixture was stirred at room temperature for 4 hours. It was then evaporated, the residue was dissolved in 0.5 ml of 1 N HCl and 0.5 ml of methanol, the solution was discharged onto a column containing a strongly acid ion exchanger (Lewatit TSW 40) and the column was washed with water and methanol/water 10:1 and eluted with methanol/water/concentrated aqueous ammonia 10:1:0.2. The eluate was evaporated in vacuo. Yield: 25 mg.

(n) N-Ethyl-1,5,7-tridesoxy-1,5-imino-D(L)-glycero-D-glucoheptitol:

500 mg of 1,5,7-tridesoxy-1,5-imino-D(L)-glycero-D-glucoheptitol were dissolved in 20 ml of methanol, 170 mg of acetaldehyde, 315 mg of sodium cyanoborohydride and 350 µl of glacial acetic acid were added and the mixture was stirred at room temperature overnight and boiled under reflux for 2 hours. For working up, 5 ml of 1 N hydrochloric acid were added, the batch was concentrated, the residue was discharged onto 30 ml of a strongly acid ion exchanger (Lewatit TSW 40) and the ion exchanger was washed with water and methanol/water 10:1 and eluted with methanol/water/ammonia 10:1:1. After concentration the eluate in a rotary evaporator, 500 mg of the desired compound were obtained. Mass spectrum: m/e=160(100%, $M^+$—$CH_3$—CH—OH).

EXAMPLE 2

The following N-alkyl derivatives of 1,5,7-tridesoxy-1,5-imino-D(L)-glycero-D-glucoheptitol were prepared in an analogous manner to Example 1, the acetaldehyde in the reaction being replaced by the aldehyde indicated:

(a) 1,5,7-Tridesoxy-1,5-imino-N-propyl-D(L)-glycero-D-glucoheptitol, aldehyde used: propionaldehyde. Mass spectrum: m/e=174 (100%, $M^+$—$CH_3$—CHOH).

(b) 1,5,7-Tridesoxy-1,5-imino-N-hexyl-D(L)-glycero-D-glucoheptitol, aldehyde used: hexanal. Mass spectrum: m/e=216 ($M^+$—$CH_3CHOH$).

(c) 1,5,7-Tridesoxy-1,5-imino-N-(2-propen-1-yl)-D(L)-glycero-D-glucoheptitol, aldehyde used: acrolein. Mass spectrum: m/e=172 (60%, $M^+$—$CH_3$—CHOH), 41 (100%, $CH_2$—CH=$CH_2$).

(d) N-(2-Buten-1-yl)-1,5,7-tridesoxy-1,5-imino-D(L)-glycero-D-glucoheptitol, aldehyde used: crotonaldehyde. Mass spectrum: m/e=186 (70%, $M^+$—$CH_3$—CHOH), 55 (100%, $CH_2$—CH=CH—$CH_3$).

(e) 1,5,7-Tridesoxy-1,5-imino-N-(2,4-hexadien-1-yl)-D(L)-glycero-D-glucoheptitol, aldehyde used: sorbaldehyde. Mass spectrum: m/e=212 (70%, $M^+$—$CH_3$—CHOH), 81 (100%, $CH_2CH$=CH—CH—$CH_3$).

(f) N-Cinnamyl-1,5,7-tridesoxy-1,5-imino-D(L)-glycero-D-glycoheptitol, aldehyde used: cinnamaldehyde. Mass spectrum: m/e=248 (30%, $M^+$—$CH_3$-CH—OH), 117 (100%, $CH_2$—CH=CH—$C_6H_5$).

(g) 1,5,7-Tridesoxy-1,5-imino-N-(2-phenoxyethyl)-D(L)-glycero-D-glucoheptitol, aldehyde used: phenoxyacetaldehyde.

(h) 1,5,7-Tridesoxy-N-ethyl-1,5-imino-D(L)-glycero-D-glucoheptitol, aldehyde used: acetaldehyde. Mass spectrum: m/e=160 (100%, $M^+$—$CH_3CHOH$).

(i) N-Butyl-1,5,7-tridesoxy-1,5-imino-D(L)-glucero-D-glucoheptitol, aldehyde used: butanal. Mass spectrum: m/e=188 (100%, $M^+$—$CH_3$—CHOH).

(j) 1,5,7-Tridesoxy-1,5-imino-N-(2-phenylethyl)-D(L)-glycero-D-glucoheptitol, aldehyde used: phenylacetaldehyde. Mass spectrum: m/e=250 (100%, $M^+$—$CH_3$—CHOH), 188 (30%), 146 (30%).

(k) N-Cinnamyl-1,5,7-tridesoxy-1,5-imino-D(L)-glycero-D-glucoheptitol:

500 mg of 1,5,7-tridesoxy-1,5-imino-D(L)-glycero-D-glucoheptitol, 5.2 ml of dimethylformamide, 600 mg of potassium carbonate and 770 mg of cinnamyl bromide were stirred at room temperature for 3 hours. The salts were then filtered off, 10 ml of water were added to the filtrate and the mixture was extracted twice with ether. The aqueous phase was concentrated in a rotary evaporator, the residue was extracted by stirring with acetone, the precipitated was separated off, the filtrate was evaporated and the residue was purified by column chromatograhy on 100 g of silica gel with chloroform-/methanol 8:2.

The following compounds were prepared in an analogous manner: 1,5,7-tridesoxy-1,5-imino-N-(2,4-hexadien-1-yl)-D(L)-glycero-D-glucoheptitol, using sorbyl bromide, and N-(2-buten-1-yl)-1,5,7-tridesoxy-1,5-imino-D(L)-glycero-D-glucoheptitiol, using crotonyl bromide.

EXAMPLE 3

(a) 2-α-Hydroxyethyl-3,4,5-trihydroxypiperidine

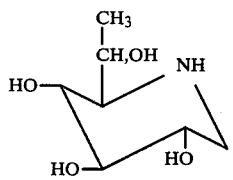

2.0 g of N-benzoyl-2-α-hydroxyethyl-3,4,5-tri-O-benzyl-3,4,5-trihydroxypiperidine in 6 ml of absolute tetrahydrofurane were slowly added dropwise to a solution of 2.0 g of sodium in 13.5 ml of liquid ammonia and 5 ml of absolute tetrahydrofurane at −70° C. The mixture was stirred at −70° C. for 4 hours and at −40° C. for 1 hour. 5 g of NH$_4$Cl were then added and the ammonia was evaporated off overnight. The residue was extracted by stirring with ethanol, the salts were filtered off and the solution was concentrated to dryness. The residue was chromatographed over a column filled with silica gel. The column was eluted first with CHCl$_3$/CH$_3$OH 4:1 and then with ether/CH$_3$OH/25% strength NH$_3$ 5:6:2. 150 mg of crude product were obtained. For further purification, this product was discharged onto a column filled with Amberlite IR 120 (H$^\oplus$ form). The column was eluted first with water and then with 2% strength ammonia. Yield: 100 mg of 2-α-hydroxyethyl-3,4,5-trihydroxypiperidine as a resin.

(b) N-Benzoyl-2-α-hydroxyethyl-3,4,5-tri-O-benzyl-3,4,5-trihydroxypiperidine

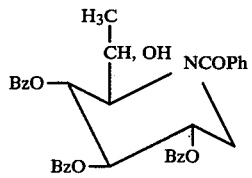

2.6 g of N-benzoyl-3,4,5-tri-O-benzyl-3,4,5-dihydroxy-piperidine-2-aldehyde in 25 ml of ether were added dropwise to a Grignard solution of 1.03 g of Mg filings and 2.26 ml of CH$_3$I in 5 ml of absolute ether at room temperature. The mixture was warmed under reflux for 2 hours. It was then reacted with NH$_4$Cl solution and acidified with dilute HCl. The ether phase was separated off and the mixture which remained was extracted 3 time with ether. The combined ether solutions were dried and concentrated. The residue was chromatographed over a silica gel column using chloroform as the mobile phase. Yield: 2 g of N-benzoyl-2-α-hydroxyethyl-3,4,5-tri-O-benzyl-3,4,5-trihydroxypiperidine as a resin.

(c) N-Benzoyl-3,4,5-tri-O-benzyl-3,4,5-trihydroxypiperidine-2-aldehyde

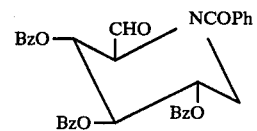

2.685 g of N-benzoyl-2-hydroxymethyl-3,4,5-tri-O-benzyl-3,4,5-trihydroxypiperidine and 0.25 g of crystalline orthophosphoric acid were added to 3.125 g of dicyclohexylcarbodiimide in 4.4 ml of absolute dimethylsulphoxide and 2.5 ml of benzene at 20° C., whilst stirring. The temperature was kept at room temperature and the mixture was subsequently stirred for 3 hours. 1 g of oxalic acid was then added, and after 30 minutes 25 ml of ethyl acetate were added. The precipitate was separated off and rinsed with ethyl acetate. The combined ethyl acetate solutions were washed first with saturated NaHCO$_3$ solution and then with saturated sodium chloride solution. The ethyl acetate solution was dried over MgSO$_4$ and the solvent was removed. 2.6 g of N-benzoyl-3,4,5-tri-O-benzyl-3,4,5-trihydroxypiperidine-2-aldehyde were obtained as a resin.

(d) N-Benzoyl-2-hydroxymethyl-3,4,5-tri-O-benzyl-3,4,5-trihydroxypiperidine

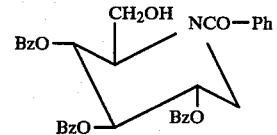

1.84 g of N,7-O-cyclocarbonato-2-hydroxymethyl-3,4,5-tri-O-benzyl-3,4,5-trihydroxypiperidine in 25 ml of absolute tetrahydrofurane were added dropwise to a Grignard solution of 10.3 g of Mg filings and 6.28 g of bromobenzene in 5 ml of absolute tetrahydrofurane and the mixture was stirred at 40° C. for 2 hours. It was then poured onto 100 ml of ice-water and rendered neutral with NH$_4$Cl and dilute HCl. The mixture was extracted with CHCl$_3$ and the chloroform solution was dried and concentrated. For crystallisation, ether was added to the residue. Yield: 1.2 g of N-benzoyl-2-hydroxymethyl-3,4,5-tri-O-benzyl-3,4,5-trihydroxypiperidine of melting point: 104°–106° C.

(e) N-Benzoyl-2-hydroxymethyl-3,4,5-tri-O-benzyl-3,4,5-trihydroxypiperidine 28 g of N-benzoyl-7-O-trityl-3,4,5-tri-O-benzyl-2-hydroxymethyl-3,4,5-trihydroxypiperidine were dissolved in 200 ml of 80% strength acetic acid and the solution was heated to 60°–70° C. for 4 hours. After cooling, triphenylcarbinol which had precipitated was filtered off. The mother liquor was concentrated in vacuo and methanol was added to the residue. The triphenylcarbinol which had precipitated was filtered off and the mother liquor was again concentrated to dryness. The residue was chromatographed over a column filled with silica gel. The column was eluted first with CHCl$_3$ and then with CHCl$_3$/MeOH 98:2. Yield:

11.3 g of N-benzoyl-2-hydroxymethyl-3,4,5-tri-O-benzyl-3,4,5-trihydroxypiperidine of melting point 106° C.

(f)
N,7-O-Cyclocarbamato-2-hydroxymethyl-3,4,5-tri-O-benzyl-3,4,5-trihydroxypiperidine

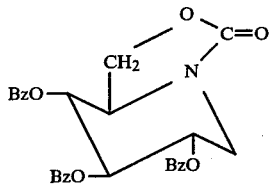

9.8 g of KOH powder and 2.9 g of N,7-O-cyclocarbamato-2-hydroxymethyl-3,4,5-trihydroxypiperidine in 100 ml of dimethylsulphoxide were heated to 60° C. for 30 minutes, whilst stirring. 17.6 ml of benzyl chloride were then added dropwise at 60° C. The mixture was stirred at 60° for a further 30 minutes. The dimethylsulphoxide was then distilled off using an oil pump. The residue was introduced into ice-water and the aqueous phase was rendered neutral with concentrated HCl. The mixture was then extracted with chloroform. The chloroform solution was dried and concentrated. The residue was chromatographed over a column filled with silica gel (eluting agent: $CHCl_3$/MeOH 40:1). Yield: 4.6 g of N,7-O-cyclocarbamato-2-hydroxymethyl-3,4,5-tri-O-benzyl-3,4,5-trihydroxypiperidine. The substance became crystalline on trituration with cyclohexane or with a little methanol. Melting point: 104°–105° C.

(g)
N,7-O-Cyclocarbamato-2-hydroxymethyl-3,4,5-trihydroxypiperidine

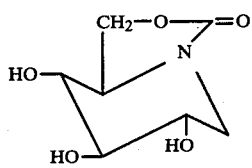

2.58 ml of chloroformic acid ethyl ester were slowly added dropwise to a mixture of 2.4 g of 1-desoxynojirimicin and 3.2 g of finely powdered $K_2CO_3$ in 50 ml of absolute dimethylformamide at 15° C., whilst stirring. The mixture was stirred at room temperature for 1 hour and was then warmed to 100° C. for 3 hours. The salts were then filtered off, the dimethylformamide solution was concentrated in vacuo and the residue was crystallised with ethanol. Yield: 2 g of N,7-O-cyclocarbamato-2-hydroxymethyl-3,4,5-trihydroxypiperidine.

For further purification, the substance could be recrystallised from ethanol/a little water. Melting point: 218° C.

(h)
N-Benzoyl-7-O-trityl-2-hydroxymethyl-3,4,5-tri-O-benzyl-3,4,5-trihydroxypiperidine

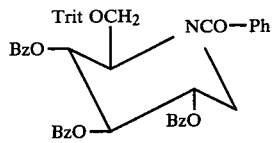

1.35 g of 80% pure NaH were stirred with 50 ml of n-hexane. The n-hexane was decanted off and replaced by 50 ml of absolute dimethylsulphoxide. The mixture was then warmed to 60°–70° C. under $N_2$ for 1 hour. After cooling, 5.1 g of N-benzoyl-7-O-trityl-2-hydroxymethyl-3,4,5-trihydroxypiperidine in 30 ml of absolute dimethylsulphoxide were added dropwise and the mixture was stirred at room temperature for 1 hour. 4.2 g of benzyl chloride in 25 ml of dimethylsulphoxide were then added dropwise and the mixture was stirred overnight. 300 ml of $CH_2Cl_2$ were added to the reaction mixture and the mixture was extracted by shaking with 200 ml of $H_2O$. The $CH_2Cl_2$ phase was washed twice more with water, dried over $Na_2SO_4$ and concentrated in vacuo. Yield: 6.5 g of crude N-benzoyl-7-O-trityl-2-hydroxymethyl-3,4,5-tri-O-benzyl-3,4,5-trihydroxypiperidine. The crude product was employed in the next reaction stage.

(i)
N-Benzoyl-7-O-trityl-2-hydroxymethyl-3,4,5-trihydroxypiperidine

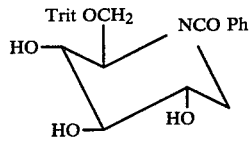

63.9 g of N-benzoyl-2-hydroxymethyl-3,4,5-trihydroxypiperidine and 79.9 g of trityl chloride in 250 ml of absolute pyridine were stirred at room temperature for 24 hours. A further 80 g of trityl chloride were then added and the mixture was stirred once again for 48 hours. The precipitate was filtered off and the mother liquor was concentrated in vacuo. The residue was dissolved in $CHCl_3$ and the chloroform solution was washed with $H_2O$. The chloroform phase was dried with $Na_2SO_4$ and concentrated in vacuo. The residue was then taken up in a little toluene. The reaction product was precipitated by adding the toluene solution dropwise to a large excess of cyclohexane. The precipitate was filtered off and dried. Yield: 90 g of crude N-benzoyl-7-O-trityl-2-hydroxymethyl-3,4,5-trihydroxypiperidine. The crude product could be further purified by trituration with ether or by recrystallisation from a little toluene. Melting point: 185°–187° C.

(j) N-Benzoyl-2-hydroxymethyl-3,4,5-trihydroxypiperidine

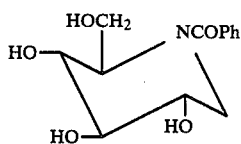

27 ml of benzoyl chloride in 300 ml of ethyl acetate were added dropwise to a solution of 30 g of 1-desoxynojirimicin in 120 ml of H$_2$O, 350 ml of CH$_3$OH and 30 ml of triethylamine at 30°–35° C. The mixture was subsequently stirred at room temperature for 1 hour and a further 15 ml of triethylamine and 13.5 ml of benzoyl chloride in 150 ml of ethyl acetate were then added dropwise at 30°–35° C. After stirring for 1 hour, the reaction mixture was evaporated to dryness in vacuo. The residue was taken up in water and the aqueous mixture was extracted with ether. The aqueous phase was again concentrated to dryness in vacuo and the residue was stirred with acetone. The triethylamine hydrochloride which has precipitated was filtered off. Residual triethylamine hydrochloride was separated off by again concentrating the acetone solution and taking up the residue in a little acetone. After removal of the solvent, the product was obtained as a resin. After thorough drying, this resin could be employed in the next stage. Yield: 56 g of crude N-benzoyl-3,4,5-trihydroxypiperidine. After standing for a relatively long period, the compound crystallised from acetone. Melting point: 159° C.

The following were prepared analogously to Examples 3a and 3b:

EXAMPLE 4

(with ethyl-magnesium iodide at room temperature)

2-α-Hydroxypropyl-3,4,5-trihydroxypiperidine

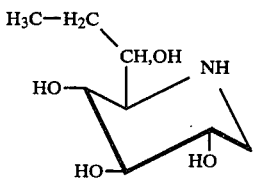

The non-crystalline product was characterised by a proton nuclear magnetic resonance spectrum at 250 MHz.
Rf value: 0.52
Rf value for 1-desoxynojirimicin: 0.31
[Pre-coated thin layer chromatography plates, Silica gel 60 F 254, Merck (Darmstadt); mobile phase: CHCl$_3$/MeOH/25% strength NH$_3$, 4:3:1].

EXAMPLE 5

(with n-butyl-lithium at −70° C.)

2-α-Hydroxypentyl-3,4,5-trihydroxypiperidine

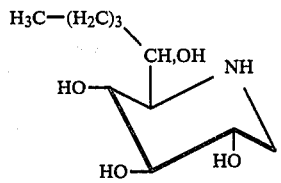

Rf value: 0.65 (chromatography conditions as in Example 4).

EXAMPLE 6

(with phenyl-magnesium bromide at −20° C.)

2-α-Hydroxybenzyl-3,4,5-trihydroxypiperidine

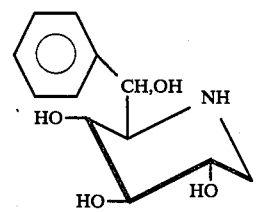

Rf value: 0.82 (chromatography conditions as in Example 4).

The present invention also comprises pharmaceutically acceptable bioprecursors of the active compounds of the present invention.

For the purpose of this specification the term 'pharmaceutically acceptable bioprecursors' of an active compound of the invention means a compound having a structural formula different from the active compound but which nonetheless, upon administration to a warm-blooded animal is converted in the patient's body to the active compound.

What is claimed is:

1. A compound which is 2-hydroxyalkyl-3,4,5-trihydroxypiperidine of the formula

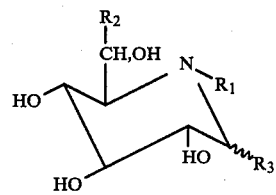

in which
R$_1$ denotes a hydrogen atom
R$_2$ denotes a C$_1$ to C$_{10}$ alkyl, C$_2$ to C$_6$ alkenyl or C$_4$ to C$_{10}$ alkadienyl radical which is optionally substituted by hydroxyl, C$_1$ to C$_4$ alkoxy or phenyl, which can in turn be substituted by C$_1$ to C$_4$ alkyl, C$_1$ to C$_4$ alkoxy, halogen, nitro or cyano, or denotes a phenyl radical which is optionally substituted by C$_1$ to C$_4$ alkyl, C$_1$ to C$_4$ alkoxy, halogen, nitro or cyano, and
R$_3$ denotes a hydrogen atom or a sulpho or hydroxyl group.

2. A compound according to claim 1, in which R$_1$ denotes a hydrogen atom
R$_3$ has the same meaning as in claim 1.

3. A compound according to claim 2 in which R$_1$ denotes a hydrogen atom.

4. A compound according to claim 1, in which $R_1$ denotes a hydrogen atom, $R_2$ denotes a methyl or a ethyl radical and $R_3$ denotes a hydrogen atom.

5. A compound according to claim 1, in which $R_1$ denotes a hydrogen atom, $R_2$ denotes a methyl radical and $R_3$ denotes a sulpho or hydroxyl radical.

6. A compound according to claim 1, in which $R_1$ denotes a hydrogen atom, $R_2$ denotes a methyl radical and $R_3$ denotes a hydrogen atom.

7. A compound according to claim 1 which is 2-α-hydroxypropyl-3,4,5-trihydroxypiperidine.

8. A compound according to claim 1 which is 2-α-hydroxypentyl-3,4,5-trihydroxypiperidine.

9. A compound according to claim 1 which is 2-α-hydroxybenzyl-3,4,5-trihydroxypiperidine.

10. A pharmaceutical composition containing as an active ingredient an amount effective for the treatment of adiposity, diabetes or hyperlipoproteinaemia of a compound according to claim 1, in admixture with an inert pharmaceutical carrier.

11. A pharmaceutical composition of claim 10 in the form of a sterile or physiologically isotonic aqueous solution.

12. A composition according to claim 10 or 11 containing from 0.1 to 99.5% by weight of the said active ingredient.

13. A medicament in dosage unit form comprising an amount effective for the treatment of adiposity, diabetes or hyperlipoproteinaemia of a compound according to claim 1 together with an inert pharmaceutical carrier.

14. A medicament of claim 13 in the form of tablets, pills, dragees, capsules, ampoules, or suppositories.

15. A method of combating disorders of carbohydrate metabolism and/or lipid metabolism in warm-blooded animals which comprises administering to the animals an α-glucoside hydrolase inhibiting amount of an active compound according to claim 1 either alone or in admixture with an inert pharmaceutical carrier.

16. A method according to claim 15 in which the active compound is administered in an amount of 0.05 to 10 mg per kg body weight per day.

17. A pharmaceutical composition according to claim 11 containing as an active ingredient 2-α-hydroxypropyl-3,4,5-trihydroxypiperidine.

18. A pharmaceutical composition according to claim 11 containing as an active ingredient 2-α-hydroxypentyl-3,4,5-trihydroxypiperidine.

19. A pharmaceutical composition according to claim 11 containing as an active ingredient 2-α-hydroxybenzyl-3,4,5-trihydroxypiperidine.

* * * * *